US008462392B2

(12) United States Patent
Loeb et al.

(10) Patent No.: US 8,462,392 B2
(45) Date of Patent: Jun. 11, 2013

(54) SYSTEM AND METHOD FOR MULTI-RESOLUTION INFORMATION FILTERING

(75) Inventors: Shoshana K. Loeb, Philadelphia, PA (US); Euthimios Panagos, Madison, NJ (US)

(73) Assignee: Telcordia Technologies, Inc., Piscataway, NJ (US)

( * ) Notice: Subject to any disclaimer, the term of this patent is extended or adjusted under 35 U.S.C. 154(b) by 707 days.

(21) Appl. No.: 12/756,568

(22) Filed: Apr. 8, 2010

(65) Prior Publication Data

US 2011/0090540 A1    Apr. 21, 2011

Related U.S. Application Data

(60) Provisional application No. 61/233,642, filed on Aug. 13, 2009.

(51) Int. Cl.
 *H04N 1/00* (2006.01)
 *G06F 17/30* (2006.01)
(52) U.S. Cl.
 USPC .......................... 358/403; 707/723; 707/732
(58) Field of Classification Search
 USPC ........... 358/403, 448, 451; 707/723, 732–734
 See application file for complete search history.

(56) References Cited

U.S. PATENT DOCUMENTS

| 6,070,133 | A | 5/2000 | Brewster et al. | |
|---|---|---|---|---|
| 6,389,169 | B1 | 5/2002 | Stark et al. | |
| 6,968,332 | B1 | 11/2005 | Milic-Frayling et al. | |
| 7,088,866 | B2 | 8/2006 | Andrew | |
| 7,565,036 | B2 | 7/2009 | Marriott et al. | |
| 2003/0018659 | A1* | 1/2003 | Fuks et al. | 707/500 |
| 2004/0169870 | A1 | 9/2004 | Ahmed et al. | |
| 2005/0021517 | A1* | 1/2005 | Marchisio | 707/4 |
| 2006/0101017 | A1 | 5/2006 | Eder | 707/7 |
| 2006/0218114 | A1* | 9/2006 | Weare et al. | 707/1 |
| 2007/0201752 | A1* | 8/2007 | Gormish et al. | 382/232 |
| 2009/0052736 | A1 | 2/2009 | Kacker | |
| 2009/0187550 | A1* | 7/2009 | Mowatt et al. | 707/5 |
| 2011/0082848 | A1* | 4/2011 | Goldentouch | 707/706 |
| 2011/0264641 | A1* | 10/2011 | Yang et al. | 707/728 |
| 2012/0310928 | A1* | 12/2012 | Ray et al. | 707/728 |

OTHER PUBLICATIONS

PCT International Search Report, Oct. 1, 2010.

* cited by examiner

*Primary Examiner* — Kimberly A Williams
(74) *Attorney, Agent, or Firm* — Philip J. Feig

(57) ABSTRACT

A method for ranking a plurality of documents relevant to a user profile comprises determining a high resolution representation for the user profile, computing a high resolution representation for each document, calculating a rank for each document based on the high resolution representation of the document and the high resolution representation of the user profile, recalculating the rank for each document based on a lower resolution representation of the document and/or a lower resolution representation of the user profile when the rank of each document is not satisfactory, and outputting a number of the plurality of documents sorted by the rank of each document, when the rank is satisfactory. The high resolution representation can be a discrete wavelet transform. The lower resolution representation can be recalculated by averaging the values of the discrete wavelet transform. Outputting the number of documents can comprise displaying the documents on a device.

15 Claims, 4 Drawing Sheets

SYSTEM AND METHOD FOR MULTI-RESOLUTION INFORMATION FILTERING

CROSS REFERENCE TO RELATED APPLICATIONS

The present invention claims the benefit of U.S. provisional patent application 61/233,642 filed Aug. 13, 2009, the entire contents and disclosure of which are incorporated herein by reference as if fully set forth herein.

FIELD OF THE INVENTION

The present invention relates generally to information filtering, document ranking, and personalization.

BACKGROUND OF THE INVENTION

Existing document ranking techniques in information filtering assign ranks, such as scores, rates, or probabilities, to documents based on the relevance or similarity of these documents to user profiles. The relevance of each document to a user's profile is typically determined by either the Euclidian distance of the document from the user profile or the probability of the document being relevant to the user profile. Document ranks are computed independently for each document. In addition, rank computations treat all components of a user profile in a uniform way. Once relevant documents are identified, these documents are presented to the user in descending order based on their relevance rank.

However, presenting relevant documents to a user in decreasing document relevance order determined as discussed above does not always result in a document collection that best matches a user's information needs. For example, when many documents are assigned very similar relevance ranks and, in addition, when the user can receive only a subset of these documents, then selecting and supplying the highest ranked (in absolute terms) documents is not always the best approach.

A method is needed for ranking documents so that their relative order achieves the maximum effectiveness with respect to a user's information needs.

SUMMARY OF THE INVENTION

An inventive solution for ranking documents that were determined to be relevant to a user profile is presented. The ranking is performed in accordance with an information filtering system by comparing different resolutions of the spectral representations of these documents against different resolutions of the spectral representation of the user profile. Advantageously, this approach can be applied to existing information filtering and retrieval systems in a straightforward manner.

The inventive method for ranking a plurality of documents relevant to a user profile comprises steps of determining a high resolution representation for the user profile, computing a high resolution representation for each document of the plurality of documents, calculating a rank for each document based on the high resolution representation of the document and the high resolution representation of the user profile, recalculating the rank for each document based on a lower resolution representation of the document and/or a lower resolution representation of the user profile when the rank of each document is not satisfactory, and outputting a number of the plurality of documents sorted by the rank of each document, when the rank is satisfactory. In one embodiment, the documents are obtained in response to a query. In one embodiment, the high resolution representation for each document and for the user profile is a discrete wavelet transform. In one embodiment, the lower resolution representation for each document is recalculated by averaging the values of the discrete wavelet transform for each document. In one embodiment, outputting the number of documents comprises displaying the documents on a device and the number of documents is based on size of the device displaying the documents.

A program storage device readable by a machine, tangibly embodying a program of instructions executable by the machine to perform methods described herein may be also provided.

BRIEF DESCRIPTION OF THE DRAWINGS

The invention is further described in the detailed description that follows, by reference to the noted drawings by way of non-limiting illustrative embodiments of the invention, in which like reference numerals represent similar parts throughout the drawings. As should be understood, however, the invention is not limited to the precise arrangements and instrumentalities shown. In the drawings.

DETAILED DESCRIPTION

An inventive system and method for ranking documents that were determined, in accordance with an information filtering system, to be relevant to a user profile by comparing different resolutions of the spectral representations of these documents against different resolutions of the spectral representation of the user profile is presented. By comparing spectral representations of information at different resolution levels against different resolutions of a user's profile, document relevance ranks can be computed that better match a user's information needs, as expressed in the user profile, than existing approaches.

The novel solution relies on spectral representations of documents and user profiles. Such representation can be obtained using different techniques and tools. One such tool is discrete wavelet transforms (DWT). DWT is a mathematical tool that allows the hierarchical decomposition of "signals" into different resolution components. Documents and profiles can be converted into "signals" on which wavelet transform or DWT can be applied. One such conversion can be done as follows:

Split each document into several sections;

Compute number of times each term (i.e., word) appears in each section;

For each term, create a sequence of values based on the computed number of times each term appears (term signal);

Assign weights to computed term signals in order to reduce the impact of certain documents and terms to the overall document score;

Compute the DWT on the resulting term signals.

Figure 1:
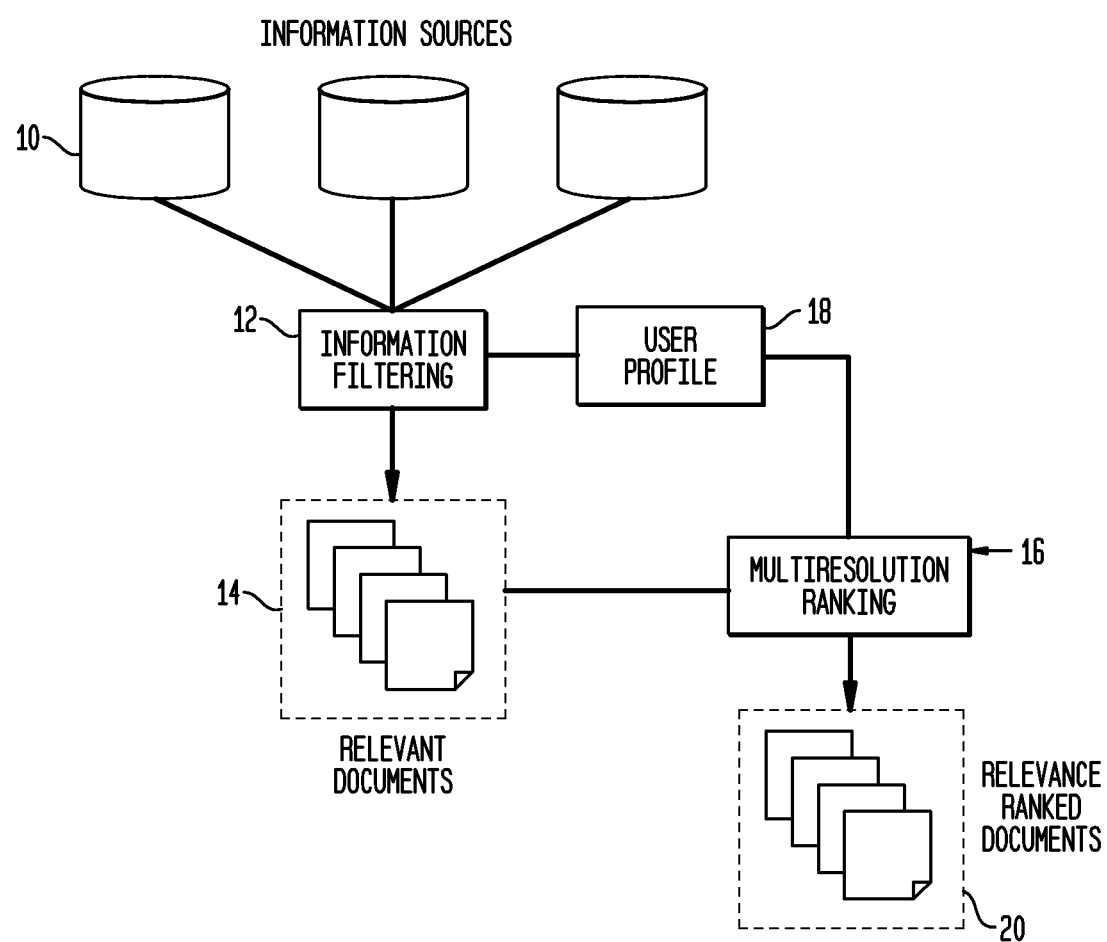
FIG. 1 shows high-level architecture of multiresolution ranking.

FIG. 1 shows the overall architecture of the present invention. In this figure, an existing information filtering approach is assumed for identifying documents that are relevant to a user profile. Initially, a query or request for information is submitted. In accordance with this submission or request, information from sources 10 is examined. Information filter 12, which can be any of various information filtering methods, identifies relevant documents 14 from the sources 10. Information filter 12 may operate by document ranking techniques such as assigning ranks, scores, rates, or probabilities to documents 14 from sources 10 based on the relevance or similarity of these documents to the initial query and/or the user's profile.

Once these documents 14 have been identified, the inventive multiresolution ranking system 16 will rank these documents based on how well they match the user's information needs. The multiresolution ranking system 16 receives as input the relevant documents 14 and the user profile 18. Relevant ranked documents 20 are output from the system 16. These documents 20 can be output as display on a device (not shown). The novel ranking approach is based on comparing different spectral resolutions of these documents against the user's profile.

An example of how these spectral comparisons are carried out at different resolutions is presented in FIGS. 2-5. In this example, assume that Haar wavelets are being used for the spectral representation of documents and user profiles. However, any means for spectral representation can be used.

In order to better understand the figures, a simple example is provided illustrating how the Haar wavelet transform works. Assume that the signal for a specific term is represented by the vector [2,4,6,8,8,6,4,2]. This signal corresponds to the highest resolution representation of the term. To obtain a lower resolution, average the signal values pair-wise and, in addition, compute the detail coefficients required for restoring the original data, e.g., the difference between second pair value and pair average. By applying this averaging technique again on the computed averages, another, lower resolution representation of the term is computed.

The following table illustrates the four Haar wavelet resolutions (averages & coefficients) for the term signal [2,4,6,8, 8,6,4,2]. In this table, resolution 3 corresponds to the highest resolution for the term signal (e.g., no information is lost). The average values included in the resolution 2 row correspond to a lower resolution of the term signal. Here, the information in the original term signal is approximated.

| Resolution | Averages | Coefficients |
|---|---|---|
| 3 | [2, 4, 6, 8, 8, 6, 4, 2] | |
| 2 | [3, 7, 7, 3] | [−1, −1, 1, 1] |
| 1 | [5, 5] | [−2, 2] |
| 0 | [5] | [0] |

Figure 2:
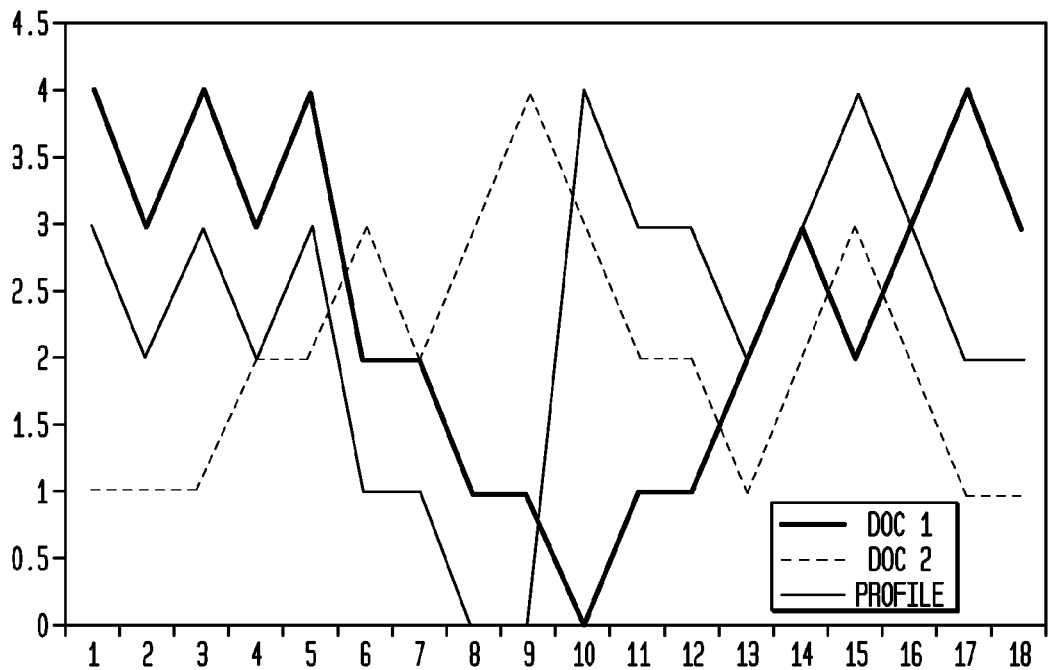
FIG. 2 shows high resolution representation of two documents and user profile based Haar wavelet representation of document and user profile.

FIG. 2 illustrates a spectral representation of two documents, Doc 1 (solid line) and Doc 2 (dashed line), and a user's profile 18, shown as user profile signal (red line). In this representation, all three signals are shown in their highest resolution. Using this figure, one cannot easily determine which of the two documents should be ranked higher.

Figure 3:
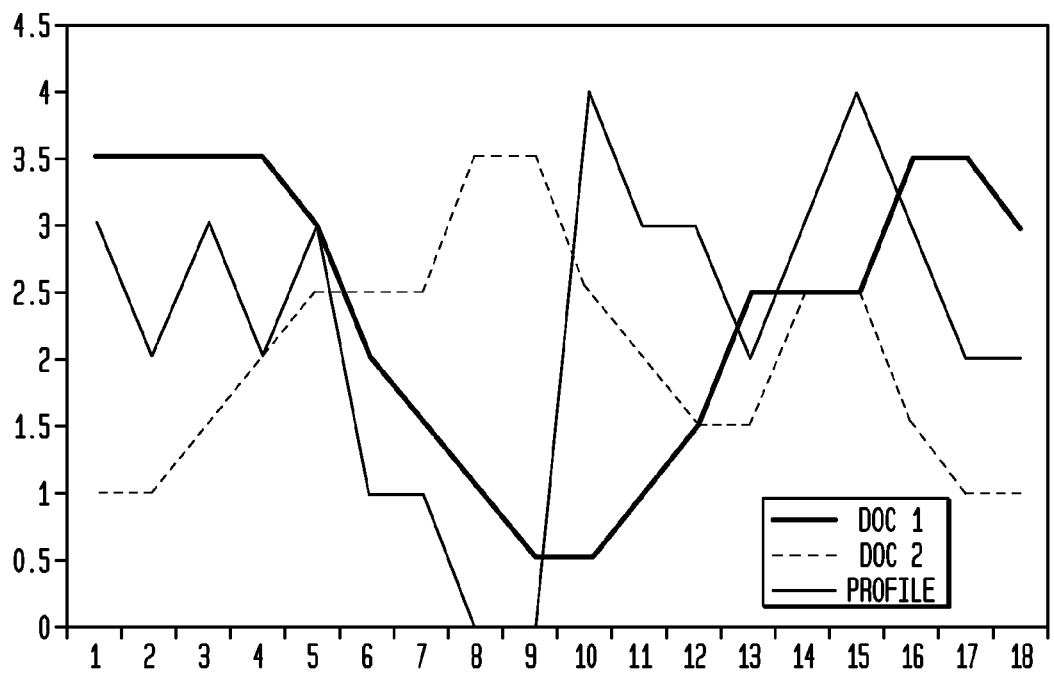
FIG. 3 shows lower resolution representation of the two documents and high resolution of user profile from FIG. 2.

FIG. 3 illustrates a lower resolution of Doc 1 (solid line) and Doc 2 (dashed line) signals, and compares these representations against the full resolution of the user profile signal (red line). As in the previous case shown in FIG. 2, it is not obvious which of the two documents is "closer" to the user profile 18 so that it is not clear which document can or should be ranked higher.

Figure 4:
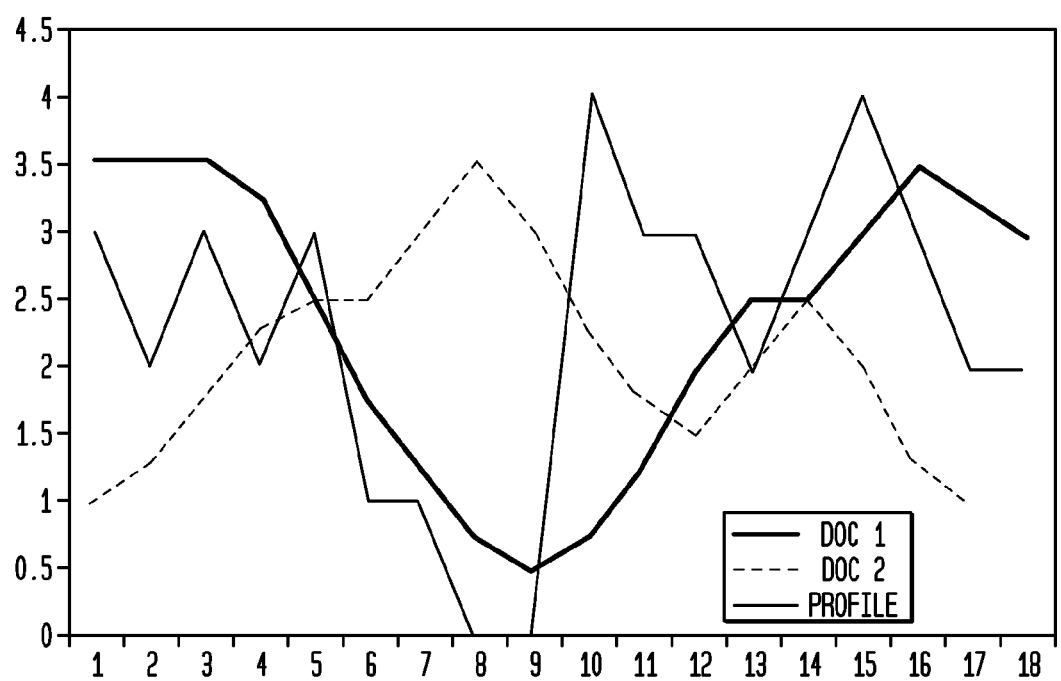
FIG. 4 shows low resolution representation of the two documents and high resolution of user profile from FIG. 2.

FIG. 4 illustrates an even lower resolution of Doc 1 (solid line) and Doc 2 (dashed line) signals, and compares these representations against the full resolution of the user profile signal (red line). This figure shows that Doc 1 exhibits behavior similar to the user profile signal. Therefore, Doc 1 seems to be a better match for the user profile 18 than Doc 2 and, thus, it should be ranked higher than Doc 2.

Figure 5:
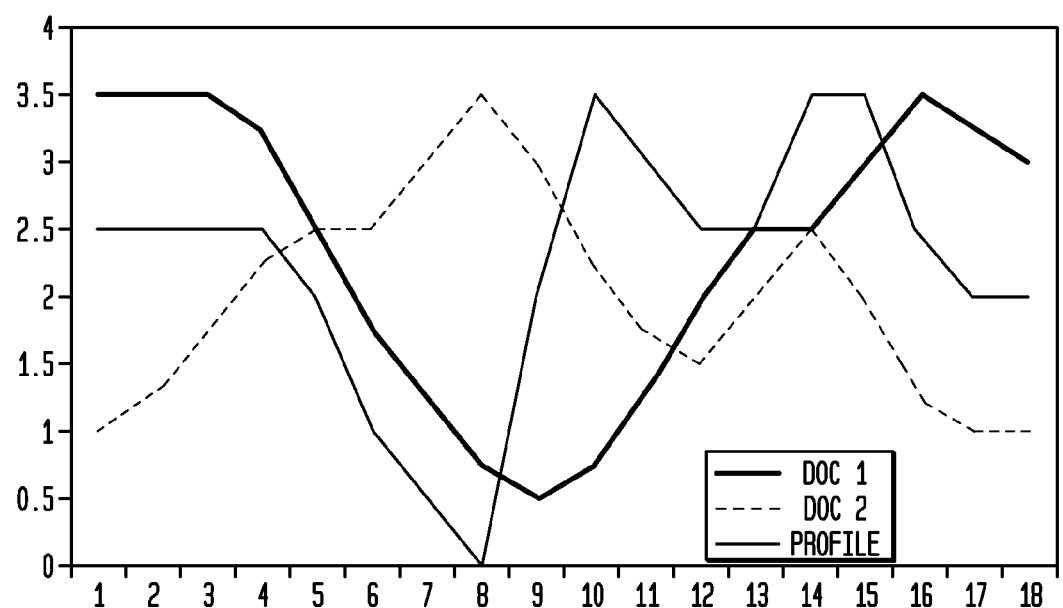
FIG. 5 shows low resolution representation of the two documents and lower resolution of user profile from FIG. 2.

To further verify that Doc 1 should be ranked higher than Doc 2 in terms of its relevance to the user profile, the low resolution of Doc 1 (solid line) and Doc 2 (dashed line) signals shown in FIG. 4 can be compared to a low resolution of the user profile signal (red line). This comparison is shown in FIG. 5. From this comparison, it is obvious that Doc 1 should be ranked higher than Doc 2.

Figure 6:
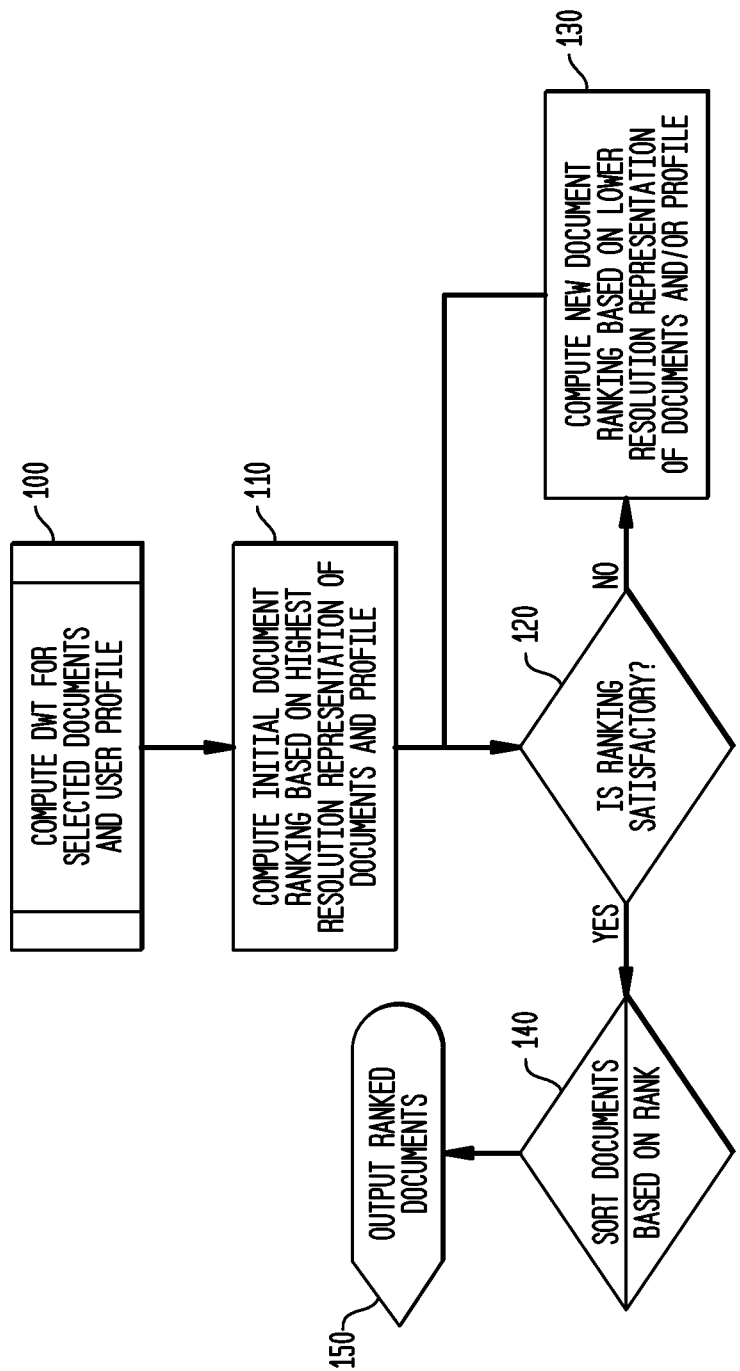
FIG. 6 shows high-level flow of multiresolution document ranking.

FIG. 6 shows the high-level flow of the multiresolution document ranking approach. In step 100, compute the wavelet transforms or DWTs for the user profile 18 and all the relevant documents 14 selected by the information filtering system 12. Note that such computations may not have to wait until the information filtering system identifies all relevant documents; instead, these computations can be performed as documents are identified. Further, the wavelet transform for the user profile 18 can be performed at any time.

In step 110, compute an initial document ranking based on a high resolution spectral, e.g., wavelet, representation of documents and user profile. In step 120, determine whether the current document ranking is satisfactory. Different criteria may be used for making this decision, such as the distance between documents being greater than a specific threshold. If the current document ranking is not satisfactory, e.g., not within a predetermined threshold (step 120=NO), a new document ranking is computed in step 130 using a lower resolution representation of the documents and/or the user profile. If the current document ranking is satisfactory (step 120=YES), step 140 sorts the documents according to their ranks and step 150 outputs the ranked documents.

One or more of the documents that are output can be displayed on a device, such as a computer monitor, a handheld device, a laptop computer, etc. In one embodiment, the number of documents that can be displayed is limited to a small number. For example, when the documents are displayed on a mobile device, such as a mobile telephone, the number of documents that can be displayed could be limited to one or two.

The multi-resolution properties of wavelets permit reducing the cosine computations required for computing document similarity. However, similarity computations are not restricted to cosine computations. Any two-dimensional curve similarity algorithm or an expression involving wavelet coefficients, e.g., sum of squares, etc., can be used. In addition, the inventive technique is not restricted to n-gram-based spectral representations of documents; instead, any "signal" representation of a document can be used. The inventive methodology focuses on document ranking.

In one embodiment, the signal representation of a document could be created by using only a subset of the elements, such as items/themes/words, present in the document. In one embodiment, the signal representation of a document may be based on attributes belonging to several user profiles, which may share similar properties (e.g., collaborative filtering). In one embodiment, the signal representation of a user profile may be based on attributes belonging to other user profiles as well as attributes associated with information and/or documents that received positive (or negative) feedback from the user, if any.

As will be appreciated by one skilled in the art, the present invention may be embodied as a system, method or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system.".

Various aspects of the present disclosure may be embodied as a program, software, or computer instructions embodied in a computer or machine usable or readable medium, which causes the computer or machine to perform the steps of the method when executed on the computer, processor, and/or machine. A program storage device readable by a machine, tangibly embodying a program of instructions executable by the machine to perform various functionalities and methods described in the present disclosure is also provided.

The system and method of the present disclosure may be implemented and run on a general-purpose computer or special-purpose computer system. The computer system may be any type of known or will be known systems and may typically include a processor, memory device, a storage device, input/output devices, internal buses, and/or a communications interface for communicating with other computer systems in conjunction with communication hardware and software, etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The embodiments described above are illustrative examples and it should not be construed that the present invention is limited to these particular embodiments. Thus, various changes and modifications may be effected by one skilled in the art without departing from the spirit or scope of the invention as defined in the appended claims.

What is claimed is:

1. A method of using a computer for ranking a plurality of documents relevant to a user profile, comprising steps of:
    determining a high resolution representation for the user profile;
    computing a high resolution representation for each document of the plurality of documents;
    calculating a rank for each document based on the high resolution representation of the document and the high resolution representation of the user profile;
    recalculating the rank for each document based on a lower resolution representation of the document and/or a lower resolution representation of the user profile when the rank of each document is not satisfactory; and
    outputting a number of the plurality of documents sorted by the rank of each document, when the rank is satisfactory.

2. The method according to claim 1, wherein the documents are obtained in response to a query.

3. The method according to claim 1, wherein the high resolution representation for each document and for the user profile is a discrete wavelet transform.

4. The method according to claim 3, wherein the lower resolution representation for each document is recalculated by averaging the values of the discrete wavelet transform for each document.

5. The method according to claim 1, wherein outputting the number of documents comprises displaying the documents on a device and the number of documents is based on size of the device displaying the documents.

6. A non-transitory computer readable storage medium storing a program of instructions executable by a machine to perform a method for ranking a plurality of documents relevant to a user profile, comprising:
    determining a high resolution representation for the user profile;
    computing a high resolution representation for each document of the plurality of documents;
    calculating a rank for each document based on the high resolution representation of the document and the high resolution representation of the user profile;
    recalculating the rank for each document based on a lower resolution representation of the document and/or a lower resolution representation of the user profile when the rank of each document is not satisfactory; and
    outputting a number of the plurality of documents sorted by the rank of each document, when the rank is satisfactory.

7. The program according to claim 6, wherein the documents are obtained in response to a query.

8. The computer readable medium according to claim 6, wherein the high resolution representation for each document and for the user profile is a discrete wavelet transform.

9. The computer readable medium according to claim 8, wherein the lower resolution representation for each document is recalculated by averaging the values of the discrete wavelet transform for each document.

10. The computer readable medium according to claim 6, wherein outputting the number of documents comprises displaying the documents on a device and the number of documents is based on size of the device displaying the documents.

11. A system for ranking a plurality of documents relevant to a user profile, comprising:
    a processor;
    a multiresolution ranking module operable to determine a high resolution representation for the user profile, compute a high resolution representation for each document of the plurality of documents, calculate a rank for each document based on the high resolution representation of the document and the high resolution representation of the user profile, and, when the rank of each document is not satisfactory, recalculate the rank for each document based on a lower resolution representation of the document and/or a lower resolution representation of the user profile; and an output device operable to output a number of the plurality of documents sorted by the rank of each document, when the rank is satisfactory.

12. The system according to claim 11, wherein the documents are obtained in response to a query.

13. The system according to claim 11, wherein the high resolution representation for each document and for the user profile is a discrete wavelet transform.

14. The system according to claim 13, wherein the lower resolution representation for each document is recalculated by averaging the values of the discrete wavelet transform for each document.

15. The system according to claim 11, wherein the output device displays the documents and the number of documents is based on size of the output device.

* * * * *